United States Patent [19]

Nunokawa

[11] 4,365,872
[45] Dec. 28, 1982

[54] EYE FUNDUS CAMERA HAVING WORKING DISTANCE DETECTING DEVICE

[75] Inventor: Kazuo Nunokawa, Tokyo, Japan

[73] Assignee: Tokyo Kogaku Kikai Kabushiki Kaisha, Tokyo, Japan

[21] Appl. No.: 116,815

[22] Filed: Jan. 29, 1980

[30] Foreign Application Priority Data

Jan. 30, 1979 [JP] Japan ................... 54-9542

[51] Int. Cl.³ .................... A61B 3/14; A61B 3/10
[52] U.S. Cl. .................... 351/208; 351/214; 354/62
[58] Field of Search .............. 351/7, 14, 16; 354/62

[56] References Cited

U.S. PATENT DOCUMENTS 4,257,687  3/1981  Kohayakawa ................ 351/7

Primary Examiner—John K. Corbin
Assistant Examiner—Rodney B. Bovernick
Attorney, Agent, or Firm—Brumbaugh, Graves, Donohue & Raymond

[57] ABSTRACT

Eye fundus camera having an illuminating system including a ring-shaped aperture and a ring-shaped mirror for preventing corneal reflection from entering the photographing optical system. The instrument further includes a working distance detecting device comprised of a light emitting element and a light sensitive element which are disposed at the opposite sides of and symmetrically with respect to the optical axis of the objective lens. The ring-shaped aperture in the illuminating system has masking portions along a plane corresponding to a plane which contains the optical axis of the objective lens and the light emitting and light sensitive elements.

6 Claims, 3 Drawing Figures

EYE FUNDUS CAMERA HAVING WORKING DISTANCE DETECTING DEVICE

The present invention relates to eye fundus camera and more particularly to eye fundus cameras having working distance detecting means for maintaining a correct working distance between the objective lens and the patient's eye.

In general opthalmoscopic instruments, it is very important to maintain a correct working distance between the instrument and the patient's eye. Particularly, in eye fundus cameras which are designed to observe the light as reflected at the fundus of the patient's eye, an incorrect working distance may cause a light as reflected at the corneal surface of the patient's eye to be admitted into the photographing optical system. Since the reflected light at the eye fundus is very weak, the reflected light at the corneal surface often produces a flare or like defects on the image at the image plane. Proposals have therefore been made, in order to detect the working distance between the objective lens of the eye fundus camera and the corneal surface of the patient's eye, to provide a working distance detecting device including a light emitting element at one side of the optical axis of the objective lens and a light sensing element at the other side of the optical axis in such a manner that the light from the light emitting element is directed so as to intersect the optical axis of the objective lens at a predetermined point and the light as reflected at the corneal surface is received by the light sensing element.

In general, however, for the purpose of preventing the illumination light as reflected at the corneal surface of the patient's eye from entering the photographing system, eye fundus cameras include an illumination optical system having an annular aperture in conjugate with the pupil of the patient's eye with respect to the objective lens, and an annular reflective surface located on the optical axis of the objective lens substantially in conjugate with the patient's pupil with respect to the objective lens so that the illumination light as passed through the annular aperture is focused at the annular reflective surface and then directed through the objective lens to the patient's eye. According to the arrangement of the illumination system, the illumination light as reflected at the corneal surface passes outside the circle of the objective lens and is prevented from entering the photographing optical system. In case of such eye fundus cameras, difficulties have been encountered in providing the aforementioned working distance detecting device since the light sensing element is located in the path of the illumination light as reflected at the corneal surface. The problem may be eliminated by increasing the diameter of the annular aperture so as to provide an increased space between the illumination light bundle and the observation light bundle. However, the solution is not practical since it will cause a decrease in the intensity of the observation light.

It is therefore an object of the present invention to provide an eye fundus camera which includes a working distance detecting device but does not have the aforementioned problems.

Another object of the present invention is to provide an eye fundus camera which includes a working distance detecting device having light sensing means located at an area masked from the illumination light.

According to the present invention, the above and other objects can be accomplished by an eye fundus camera including objective lens means having an optical axis and adapted to be placed a distance from a patient's eye, an illumination system for projecting an illumination light through the objective lens means, an imaging optical system for focusing a light bundle as reflected at fundus of the patient's eye on an imaging plane, said illumination system including annular aperture means having a substantially ring-shaped light transparent portion in conjugate with pupil of the patient's eye with respect to the objective lens means and reflecting means having a substantially ring-shaped reflecting surface located on the optical axis of the objective lens means substantially in conjugate with the pupil of the patient's eye with respect to the objective lens means so that the illumination light as passed through the annular aperture means is focused on the reflecting surface of the reflecting means and then directed through the objective lens means to the patient's eye, working distance detecting means including light source means located at one side of the optical axis of the objective lens means for projecting a working distance detecting light in a plane containing the optical axis of the objective lens means so that the working distance detecting light intersect the optical axis at a point which is apart from the objective lens means by a predetermined distance and light sensing means located symmetrically with the light source means with respect to the optical axis of the objective lens means, said annular aperture means being provided, in a plane corresponding to the plane containing said light source means and said light sensing means at least at a side corresponding to a side where the light sensing means is located, with masking means for masking said transparent portion of the annular aperture means. According to the arrangement of the present invention, the light sensing means is located outside the path of the reflected light from the patient's corneal surface so that the operation of the light sensing means is not disturbed by the reflected light. The loss of the illumination light due to the masking means is very small and practically ignorable.

The above and other objects and features of the present invention will become apparent from the following descriptions of a preferred embodiment taking reference to the accompanying drawings, in which.

Figure 1:
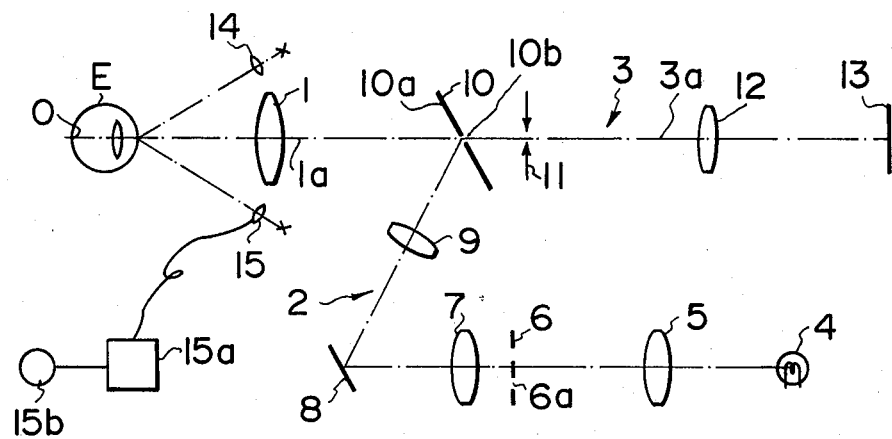
FIG. 1 is a schematic drawing showing the optical system of an eye fundus camera to which the present invention can be applied.

Referring to the drawings, particularly to FIG. 1, the optical system of the eye fundus camera shown therein includes an objective lens 1 which is adapted to be placed a distance from an eye E to be inspected. The objective lens 1 has an optical axis $1a$ on which an apertured mirror 10 is located in conjugate with the pupil of the patient's eye E with respect to the objective lens 1.

The optical system includes an illuminating system 2 comprised of a lamp 4 from which the light is passed through a condenser lens 5, a ring-shaped aperture disc 6 having a ring-shaped light transparent portion $6a$ and a lens 7 to a mirror 8 to be reflected thereby. The light reflected by the mirror 8 is then passed through a lens 9 to the apertured mirror 10 which reflects the light toward the objective lens 1. The light is then passed through the pupil of the patient's eye E to the fundus O.

The optical system further includes a photographing optical system 3 which is comprised of an aperture 11 located behind the apertured mirror 10 substantially in conjugate with the pupil of the patient's eye E with respect to the objective lens 1, and a focusing lens 12 provided behind the aperture 11 along a photographing optical axis 3a. The light reflected at the eye fundus O is therefore passed the aperture 11 and the focusing lens 12 to produce an image of the eye fundus on a photographing film plane 13.

The ring-shaped aperture 6 in the illuminating optical system 2 is located in conjugate with the pupil of the patient's eye E with respect to the objective lens 1 and the lenses 7 and 9 so that the illuminating light from the light source 4 is passed through the light transparent portion 6a of the aperture disc 6, the lens 7, the mirror 8 and the lens 9 to the apertured mirror 10. The apertured mirror 10 has an annular reflecting surface 10a and a central aperture 10b and the illuminating light is focused on the reflecting surface 10a. The illuminating light is then reflected at the surface 10a and directed toward the objective lens 1 to be projected through the lens 1 to the patient's eye E. Although not shown in the drawing, the illuminating system 2 may have two separate light sources, one for photographing and the other for visual observation as commonly adopted in the art. For further details of the optical system of the eye fundus camera, reference may be made to the application Ser. No. 35804 filed on May 4, 1979 now U.S. Pat. No. 4,235,540 and assigned to the same assignee of the present application.

The eye fundus camera shown in FIG. 1 further includes a working distance detecting device which is comprised of a light emitting element 14 such as a light emitting diode and a light sensitive element 15 which are located at the opposite sides of the objective lens 1 in a plane containing the optical axis 1a of the lens 1. The light emitting element 14 is designed to produce a light of a modulated pattern such as of a pulsating pattern and direct it to a point on the optical axis 1a of the objective lens 1, which is forwardly apart from the objective lens 1 by a distance corresponding to the working distance of the eye fundus camera. The light sensitive element 15 is located so as to receive the light from the aforementioned point on the axis 1a. It should therefore be noted that, where the objective lens 1 is at a correct working distance with respect to the patient's eye E, the light from the element 14 is reflected at the corneal surface of the eye E and received by the element 15. The light sensitive element 15 then produces an electric signal which is transmitted through a signal detecting circuit 15a to produce an output signal. The output signal may be utilized to energize an indicating device 15b such as a buzzer or an indicating light as conventional in the art.

Figure 2:
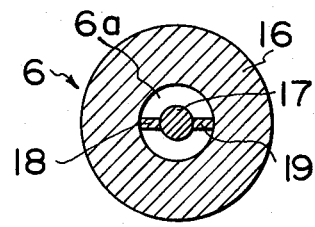
FIG. 2 is a front view of the annular aperture plate in accordance with one embodiment of the present invention; and, FIG. 3 is a view showing the relationship between the illumination light as reflected at the corneal surface and the light emitting and light sensing elements.

Referring now to FIG. 2 which shows in detail the aperture disc 6, it will be noted that the disc 6 has an outside opaque area 16 and a central opaque area 17 which are located outside and inside the transparent portion 6a, respectively. In the transparent portion 6a, there are formed masking portions 18 and 19 of suitable widths which are in diametrically opposite positions along a plane in the illumination system 2 corresponding to the plane containing the optical axis 1a of the objective lens 1 and the elements 14 and 15. It should be noted that one of the masking portions 18 and 19 may be omitted and the other may be located at the side corresponding to the side where the light sensitive element 15 is positioned.

Figure 3:
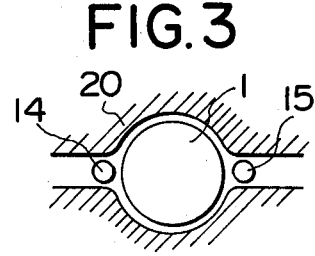

In the instrument having the ring-shaped aperture disc 6 as shown in FIG. 2, the illumination light as reflected at the corneal surface of the patient's eye E forms a pattern as shown by the reference numeral 20 in FIG. 3. It should therefore be understood that the light emitting element 14 and the light sensitive element 15 are located outside the path of the reflected light. Thus, the reflected light 20 does not have any disturbing effect on the detection of the working distance by the elements 14 and 15.

According to the feature of the present invention, the ring-shaped aperture 6a in the illumination system 2 is thus formed with masking portions 18 and 19 for preventing the illumination light as reflected at the corneal surface from being injected to the light sensitive element 15. It is therefore possible to provide an accurate detection of the correct working distance. Where the light emitting element is so designed that it produces a modulated light as described with reference to the preceding embodiment, it is readily possible to discriminate the light from the light emitting element from other light such as the light from external light source or internally reflected lights.

The invention has thus been shown and described with reference to a specific embodiment, however, it should be noted that the invention is in no way limited to the details of the illustrated arrangements but changes and modifications may be made without departing from the scope of the appended claims.

I claim:

1. Eye fundus camera including objective lens means having an optical axis and adapted to be placed a distance from a patient's eye, an illumination system for projecting an illumination light through the objective lens means, an imaging optical system for focusing a light bundle as reflected at fundus of the patient's eye on an imaging plane, said illumination system including annular aperture means having a substantially ring-shaped light transparent portion in conjugate with pupil of the patient's eye with respect to the objective lens means and reflecting means having a substantially ring-shaped reflecting surface located on the optical axis of the objective lens means substantially in conjugate with the pupil of the patient's eye with respect to the objective lens means so that the illumination light that is passed through the annular aperture means is focused on the reflecting surface of the reflecting means and then directed through the objective lens means to the patient's eye, working distance detecting means including light source means located at one side of the optical axis of the objective lens means for projecting a working distance detecting light in a plane containing the optical axis of the objective lens means so that the working distance detecting light intersects the optical axis at a point which is apart from the objective lens means by a predetermined distance and light sensing means located symmetrically with the light source means with respect to the optical axis of the objective lens means, said annular aperture means being provided, in a plane corresponding to the plane containing said light source means and said light sensing means at least at a side corresponding to a side where the light sensing means is located, with masking means for masking a portion of said transparent portion of the annular aperture means said masking means being located such that light from the illumination source is blocked by said masking means so as to not interfere with said distance detecting means.

2. Eye fundus camera in accordance with claim 1 in which said masking means includes a pair of opaque masking portions which are located at diametrically opposite portions with respect to center of the ring-shaped transparent portion of the aperture means.

3. Eye fundus camera in accordance with claim 1 in which said light source means is located at one side of the objective lens means and the light sensing means at the other side of the objective lens means.

4. Eye fundus camera in accordance with claim 1 in which said light source means is a light emitting diode for producing a modulated light.

5. Eye fundus camera in accordance with claim 4 in which said light sensing means is connected with detecting circuit means for detecting the modulated light to produce an output signal.

6. Eye fundus camera in accordance with claim 5 in which indicating means is provided for receiving said output signal of the detecting circuit means to provide an indication that the camera is at a correct working distance.

* * * * *